(12) United States Patent
Huang et al.

(10) Patent No.: US 9,353,038 B2
(45) Date of Patent: May 31, 2016

(54) METHODS FOR PREPARING FLUORINATED VINYL ETHERS

(75) Inventors: Chialang Grand Huang, Edison, NJ (US); Linas V. Kudzma, Annandale, NJ (US)

(73) Assignees: BAXTER INTERNATIONAL, INC., Deerfield, IL (US); BAXTER HEALTHCARE SA, Glattpark (Opfikon) (CH)

( * ) Notice: Subject to any disclaimer, the term of this patent is extended or adjusted under 35 U.S.C. 154(b) by 213 days.

(21) Appl. No.: 12/426,919

(22) Filed: Apr. 20, 2009

(65) Prior Publication Data

US 2010/0267995 A1    Oct. 21, 2010

(51) Int. Cl.
*C07C 41/24*    (2006.01)
*C07C 43/17*    (2006.01)

(52) U.S. Cl.
CPC ..................................... *C07C 41/24* (2013.01)

(58) Field of Classification Search
None
See application file for complete search history.

(56) References Cited

U.S. PATENT DOCUMENTS 5,886,239 A    3/1999   Kudzma et al. ............... 568/684
6,054,626 A    4/2000   Chambers et al. ............. 568/683

OTHER PUBLICATIONS

Definition of ethyl ether on p. 1 of 1 from Hawley's Condensed Chemical Dictionary, 14th Edition, 2002.*
Boaz et al., "Applications of Diethoxymethane as a Versatile Process Solvent and Unique Reagent in Organic Synthesis," Organic Process Res. & Dev., 5:127-131 (2001).
Goldberg et al., "Dose of Compound A, Not Sevoflurane, Deteiniines Changes in the Biochemical Markers of Renal Injury in Healthy Volunteers," Anesth. Analog., 88:437-445 (1999).
Huang et al., "Detailed Investigation of Luoromethyl 1,1,1,3,3,3-Hexafluoro-2-Propyl Ether (Sevoflurane) and Its Degradation Products, Part I; Synthesis of Fluorinated, Soda Lime Induced Degradation Products," J. Fluorine Chem. 45:239-253 (1989).
USP Catalog, "USP Reference Standards and Authentic Substances," p. 105, Jan.-Feb. 2009, www.usp.org.
International Search Report and Written Opinion for corresponding International Application No. PCT/US2010/031726 (Jul. 13, 2010).
International Preliminary Report on Patentability for corresponding International Application No. PCT/US2010/031726, dated Jun. 28, 2011.

* cited by examiner

*Primary Examiner* — Rosalynd Keys
(74) *Attorney, Agent, or Firm* — Marshall, Gerstein & Borun LLP

(57) ABSTRACT

A method for preparing a fluorinated vinyl ether compound comprising reacting a fluorinated ether substrate having (i) a hydrogen atom on a carbon atom that is alpha to an etheric oxygen and (ii) a fluorine atom on a carbon atom that is beta to the etheric oxygen, with an organolithium base to provide a reaction product comprising a fluorinated vinyl ether compound.

18 Claims, No Drawings

METHODS FOR PREPARING FLUORINATED VINYL ETHERS

BACKGROUND

1. Field of the Disclosure

The disclosure generally relates to methods for preparing fluorinated vinyl ethers, and more particularly to methods for preparing fluoromethyl-1,1,3,3,3-pentafluoro-2-propenyl ether (sevoflurane compound A) and other vinyl ethers corresponding to fluorinated ether anesthetic compounds.

2. Brief Description of Related Technology

Certain fluorinated ethers are useful volatile anesthetic compounds, which can be administered via inhalation. Over time, such fluorinated ether anesthetic compounds can degrade and form corresponding vinyl ether degradation products/impurities. For example, sevoflurane, a widely-used volatile anesthetic compound, often includes an amount of fluoromethyl-1,1,3,3,3-pentafluoro-2-propenyl ether ("compound A"). Compound A has been shown to induce renal injury in rats and to produce transient renal injury in humans (Goldberg, et al., *Anesth. Analg.*, 88:437-45 (1999)). Thus, it is desirable to ensure that the quantity of this vinyl ether is sufficiently low to ensure the quality of the anesthetic drug product. Similarly, it is desirable to ensure that the content of vinyl ether degradation products is below prescribed limits in other fluorinated ether-containing anesthetic compounds including but not limited to sevomethyl ether, chlorosevomethyl ether, isoflurane, desflurane, and difluoromethyl 2,2,2-trifluoroethyl ether. Typically, the amount of impurity in a sample of a fluorinated ether-containing anesthetic compound is determined by gas chromatography (GC) or other comparative spectroscopic technique using a pure reference standard. While compound A is commercially available, it is expensive. Additionally, vinyl ether compounds corresponding to other fluorinated ether-containing anesthetics are not commercially available. Accordingly, an efficient synthetic method to prepare fluorinated vinyl ether compounds is desirable.

Fluorinated ethers, however, are very reactive, and thus there are not many efficient methods for their synthesis. Huang, et al., *J. Fluorine Chem.*, 45:239-253 (1989) describes the synthesis of compound A through the dehydrofluorination of sevoflurane using various bases. When sodium hydride with a triethylamine-boron complex was used as the base, no reaction occurred. Other bases such as potassium hydroxide, potassium tert-butoxide, sec-butyl lithium, tert-butyl lithium, phenyl lithium, and lithium diisopropylamide resulted in incomplete reactions with low yields when performed at −78° C. to 80° C. While a complete reaction was achieved using methyl lithium as the base at −78° C., Huang found the reaction to be unsuitable because it was difficult to isolate the desired vinyl ether product and the reaction was very exothermic and thus not capable of being scaled up even at the very low temperature of −78° C. As a result of these studies, Huang used lithium bis-(trimethylsilyl)amide as the base (observing product yields of 50-60% using preparative GC to isolate the material to the required purity). The disclosed method is not suitable for the large scale synthesis and isolation of sevoflurane compound A, however, because it is not practical to use preparative GC to isolate large quantities of product.

When lithium bis-(trimethylsilyl)amide was used to prepare the previously described vinyl ethers and fractional distillation was used to isolate the desired vinyl ether product, chemical conversion was not satisfactory and a laborious, repeated distillation process was necessary to achieve desired purity. The lengthy and cumbersome purification process was necessary because the crude product underwent further reactions with other components present in the reaction medium to generate difficult to remove side products. For example, as described in comparative example 1, the preparation of compound A using a 1.0 M solution of lithium bis-(trimethylsilyl)amide in THF as the base often required more than five months to obtain material with the desired 99% purity at a yield of only 10-20%.

SUMMARY

In one aspect, a method for preparing a fluorinated vinyl ether compound comprises reacting a fluorinated ether substrate having (i) a hydrogen atom on a carbon atom that is alpha to an etheric oxygen and (ii) a fluorine atom on a carbon atom that is beta to the etheric oxygen, with an organolithium base to provide a reaction product comprising a fluorinated vinyl ether compound.

In a further aspect, a method for preparing fluorinated vinyl ether compounds comprises providing a fluorinated ether substrate having a hydrogen atom on a carbon atom that is alpha to an etheric oxygen, and a fluorine atom on a carbon atom that is beta to the etheric oxygen, cooling the fluorinated ether substrate to less than or equal to 5° C., adding methyl lithium dissolved in diethoxymethane to the fluorinated ether substrate to provide a reaction mixture, and removing a fluorinated vinyl ether compound from the reaction mixture.

DETAILED DESCRIPTION

The present disclosure is directed to methods for preparing fluorinated vinyl ethers. Advantageously, the disclosed methods provide for the synthesis of fluorinated vinyl ethers in relatively high purity and yield (at least relative to demonstrated synthetic methods, for example, where lithium bis(trimethylsilyl)amide is used as the base and/or THF is used as the solvent). Furthermore, the disclosed methods facilitate the production of reference standards suitable for analyzing and ensuring the quality/purity of fluorinated ether compounds which are useful as volatile anesthetics.

The methods according to the disclosure involve reacting a fluorinated ether substrate having (i) a hydrogen atom on a carbon atom that is alpha to an etheric oxygen and (ii) a fluorine atom on a carbon atom that is beta to the etheric oxygen with an organolithium base. When introduced to fluorinated ether substrates, organolithium bases promote a facile reaction to form the corresponding fluorinated vinyl ethers. Using organolithium bases for the dehydrofluorination of fluorinated ethers is particularly advantageous because the reaction proceeds quickly, fewer by-products are formed, and less volume is present for work-up (at least relative to demonstrated synthetic methods, for example, where lithium bis(trimethylsilyl)amide is used as the base and/or THF is used as the solvent). Also, purification of the resulting fluorinated vinyl ethers is relatively easy (at least relative to demonstrated synthetic methods, for example, where lithium bis(trimethylsilyl)amide is used as the base and/or THF is used as the solvent).

The fluorinated ether substrate and/or the organolithium base are typically cooled before the reaction is initiated. Preferably, the organolithium base is dissolved in an acetal solvent and added dropwise to a pre-cooled fluorinated ether substrate. The disclosed methods optionally further comprise removing the resulting fluorinated vinyl ether product by vacuum at a low temperature and/or isolating the fluorinated vinyl ether product by fractional distillation, as described in further detail below.

Fluorinated ether substrates suitable for use in the methods according to the present disclosure typically comprise a hydrogen atom on the carbon that is alpha (or α) to an etheric oxygen atom, and a fluorine atom on the carbon that is beta (or β) to the etheric oxygen atom. Representative fluorinated ethers have the structure shown, for example, in Formula I, below (wherein the alpha and beta carbons are labeled):

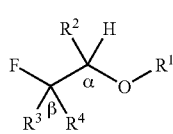

Formula I wherein $R^1$ is selected from the group consisting of alkyl and haloalkyl, for example, $C_{1-2}$ alkyl or $C_{1-2}$ haloalkyl;

$R^2$ is selected from the group consisting of H, F, Cl, alkyl (for example, $C_{1-2}$ alkyl) and haloalkyl (for example, $C_{1-2}$ haloalkyl); and, $R^3$ and $R^4$ are independently selected from the group consisting of H and F. Preferably, the alpha carbon only has a single hydrogen (and thus $R^2$ is not a hydrogen atom) as substrates having two hydrogen atoms on the carbon alpha to the etheric oxygen have been found to have low reactivity. For example, in one aspect, $R^2$ comprises F, Cl, alkyl, or haloalkyl.

As used herein, the term "alkyl" is defined as straight chained and branched hydrocarbon groups containing the indicated number of carbon atoms, typically methyl, ethyl, and straight chain and branched propyl and butyl groups. The hydrocarbon group can contain up to eight carbon atoms, for example. The term "alkyl" further includes "cycloalkyl," i.e., cyclic $C_3$-$C_8$ hydrocarbon groups, e.g., cyclopropyl, cyclobutyl, cyclohexyl, and cyclopentyl.

The term "halo" is defined herein to include fluorine, bromine, chlorine, and iodine. Thus, the term "haloalkyl" is defined as an alkyl (as defined above) further including at least one of fluorine, bromine, chlorine, and iodine (typically selected from fluorine and chlorine).

In another aspect, fluorinated ether substrates suitable for use in the methods according to the disclosure have the structure shown in Formula II:

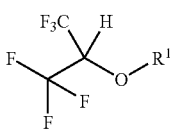

Formula II wherein $R^1$ is selected from the group consisting of alkyl and haloalkyl (e.g., R is selected from the group consisting of $CH_3$, $CH_2CH_3$, $CH_2F$, $CH_2Cl$, $CHF_2$, $CF_2Cl$, and $CHFCF_3$).

Specific representative fluorinated ether substrates suitable for use in the methods according to the disclosure include, but are not limited to, anesthetic compounds such as sevoflurane (2,2,2-trifluoro-1-[trifluoromethyl]ethyl fluoromethyl ether), sevomethyl ether(2,2,2-trifluoro-1-[trifluoromethyl]ethyl methyl ether), chlorosevomethyl ether(2,2,2-trifluoro-1-[trifluoromethyl]ethyl chloromethyl ether), isoflurane(1-chloro-2,2,2-trifluoroethyl difluoromethyl ether), desflurane(2,2,2-trifluoro-1-fluoroethyl-difluoromethyl ether), difluoromethyl 2,2,2-trifluoroethyl ether, and other fluorinated ether substrates such as chlorodifluoromethyl 2,2,2-trifluoroethyl ether, and bis-(1,2,2,2-tetrafluoroethyl)ether. Suitable fluorinated ether anesthetic compound substrates can be obtained commercially and/or prepared, for example, in accordance with the synthetic methods disclosed in U.S. Pat. Nos. 5,886,239 and 6,054,626, the contents of which are incorporated herein by reference.

The base used in the present disclosure is typically an organolithium base having a bond between a carbon atom and a lithium atom. Organolithium bases are typically avoided in chemical syntheses because they must be used with care. For example, organolithium bases must generally be added slowly to a cooled reaction mixture. Surprisingly, it has been determined that a large excess of the organolithium base (relative to the amount of the fluorinated ether substrate) can destroy the fluorinated vinyl ether product and thus decrease the yield. On the other hand, if the molar percentage of the organolithium base is too low (relative to the amount of the fluorinated ether substrate), lesser amounts of undesired side products are formed but the removal of unreacted fluorinated ether substrate can make isolation of the final product difficult. The amount of organolithium base used in the methods according to the disclosure can be between about 15 molar percent ("mol %") and about 175 mol % of the amount of the fluorinated ether substrate (according to this convention, the amount of fluorinated ether substrate is 100 mol %), for example, between about 25 mol % and about 150 mol %, between about 50 mol % and about 125 mol %, and/or between 75 mol % and 125 mol % of the fluorinated ether substrate. Typically, a slight excess of organolithium base is reacted with the fluorinated ether substrate (e.g., the base is present in an amount between about 105 mol % and about 125 mol % relative to the amount of fluorinated ether substrate).

Suitable organolithium bases include but are not limited to alkyl lithium compounds such as methyl lithium, iso-propyl lithium, n-butyl lithium, sec-butyl lithium, t-butyl lithium, and hexyl lithium, and aryl lithium compounds such as phenyl lithium, 4-chlorophenyl lithium, 4-fluorophenyl lithium, 4-trifluoromethylphenyl lithium, 4-methoxyphenyl lithium, and napthyl lithium. Typically, alkyl lithium bases having four carbon atoms or less are used because the co-products of such bases are easier to remove from the reaction mixture (e.g., methyl lithium generates methane gas) and thus make work-up simpler. Methyl lithium is also generally preferred because of it is relatively greater basicity (and hence reactivity in the dehydrofluorination reaction described herein) relative to other alkyl lithium bases.

The solvent used in the methods according to the present disclosure is typically an acetal. Such solvents are advantageously stable in the presence of strong bases such as the organolithium bases mentioned herein. Such solvents can also advantageously solvate relatively higher concentrations of the organolithium base (e.g., at least about 2.0 M, at least about 3.0 M, etc.). Additionally, the aforementioned solvents have relatively high boiling points relative to desired fluorinated vinyl ether products such as compound A and thus will not co-distill with the desired fluorinated vinyl ether product during purification. However, the boiling point of the selected solvent cannot be too high; at the relatively low temperatures typically used to conduct the reaction according to the invention, most high boiling solvents will solidify, thereby rendering the reaction mixture solid (and dangerous). Accordingly, the solvent selection is rather important for achieving good yields and desired product purity levels. Typically, the acetal solvent has a boiling point between about 65° C. and about 100° C., between about 70° C. and about 95° C., and/or between about 75° C. and about 90° C., with the proviso that the acetal solvent is generally selected such that there is a boiling point difference of at least about 10° C. between the selected solvent and the desired fluorinated ether product.

Suitable acetal solvents for use in the methods according to the disclosure include but are not limited to diethoxymethane, 1,1-diethoxyethane, 1,1-dimethoxyethane(diglyme), 1,3-dioxolane, and 2,2-dimethoxypropane. Acetal solvents having relatively low water solubility such as diethoxymethane are generally preferred because such solvents do not require drying before use in the methods according to the disclosure (residual water will react with the organolithium base). A 3.0 M solution of methyl lithium in diethoxymethane is commercially available from Sigma-Aldrich Chemicals and is a particularly convenient combination of an acetal solvent and an organolithium base for use in the methods according to the disclosure. Of course, other concentrations of organolithium bases including but not limited to between about 0.1 M and about 4.0 M, between about 0.5 M and about 3.75 M, and/or between about 1.0 M and about 3.5 M can be used (for example, about 3.0 M). As mentioned previously, other organolithium solvents and other acetal solvents are also suitable.

The methods according to the disclosure typically involve cooling the fluorinated ether substrate to a temperature below room temperature, for example, a temperature less than or equal to 5° C., between about −78° C. and about +5° C., between about −60° C. and about 0° C., and/or between about −40° C. and about 0° C., before the organolithium base is added to initiate the reaction. After cooling the substrate, a solution of the organolithium base in the acetal solvent can be added dropwise to the reaction mixture.

After addition of the organolithium base is complete, the reaction mixture can be stirred for an additional time period, for example, up to five hours, up to three hours, and/or up to one hour. Typically, the stirring takes place at a temperature between about −78° C. and about +5° C. (including the suitable temperature ranges for cooling the fluorinated ether substrate mentioned above).

The reaction can be performed under an inert atmosphere, for example, a nitrogen atmosphere or an argon atmosphere.

The resulting fluorinated vinyl ether product can be separated from the reaction mixture by vacuum and then further purified by distillation, for example, by fractional distillation. The fluorinated vinyl ether product can advantageously be isolated at a relatively high yields of at least 40%, at least 45%, at least 50%, and/or at least 55%, with a purity of at least 95%, at least 98%, and/or at least 99%.

The following examples are provided to illustrate the disclosure, but are not intended to limit the scope thereof.

EXAMPLES

Comparative Example 1

Large Scale Preparation of Sevoflurane Compound A

About 1.0 L of a 1.0 M solution of lithium bis(trimethylsilyl)amide, $LiN[Si(CH_3)_3]_2$, in THF was added gradually to a 1-L 3-neck flask containing about 181.0 grams (0.9 mols) of sevoflurane in about 100 mL of anhydrous THF. The addition was complete after approximately 1.5 hours and carried out at a temperature between about −40° C. and about −20° C. under a nitrogen atmosphere. The reaction mixture was stirred at the same temperature for about 15 minutes. A vacuum (2.5 mm Hg) applied to the reaction vessel for about 5.5 hours while the temperature of the reaction mixture was held between about −40° C. and about −20° C. afforded about 771 grams of a liquid crude product in two dry ice traps (connected in series). The crude product contained about 6% of compound A.

The same reaction was repeated 12 more times to give a total crude product weight of about 7,100 grams. The liquid was divided into 2 batches and distilled separately using a 1 inch×8 feet long vacuum jacketed silvered glass column which was packed with protruded Hastelloy metal packing and topped with an automatic splitter connected to a condenser cooled to about 0° C. Approximately 1331 grams of crude compound A was collected.

In this example the 1331 grams of crude product was combined with an additional 74 grams of crude compound A which was distilled from 1090 grams of a liquid crude product (collected from four additional reactions at the same scale described above). The combined liquid (1405 grams) contained about 60% compound A and was concentrated further on a 1 inch×4 feet long distillation apparatus similar to the one described above to remove low boiling components. About 1155 grams of liquid remained and was divided into three batches, which were separately distilled on a ½ inch×12 inch long vacuum jacketed glass column which was packed with 3 mm glass helices and topped with an automatic splitter connected to a condenser. Fractions collected with compound A purity greater than 97% were combined and distilled again using the same apparatus to afford about 291.4 grams of compound A having 99.2% purity.

The yield for >99% pure compound A was only 11.3% and it took greater than five months to obtain sevoflurane compound A at the desired purity level due to multiple and slow distillations.

Example 1a

Preparation of fluoromethyl 1,1,1,3,3-pentafluoro-2-propenyl ether ($CF_3C(=CF_2)OCH_2F$, or "Sevo Compound A")

About 140.5 grams of sevoflurane (0.703 mols) was placed in a 1-L 3-neck flask equipped with a thermocouple, an addition funnel, a magnetic stirring bar, and a nitrogen inlet, and cooled in a dry ice-acetone bath to about −31° C. About 275 mL of a 3.0 M solution of methyl lithium in diethoxymethane ($CH_3Li/CH_2(OC_2H_5)_2$, 0.825 mols of the base) was added to the sevoflurane over approximately 2.5 hours while maintaining a reaction temperature between about −30° C. and about −20° C. After addition of the methyl lithium was complete, the addition funnel was washed with a few mL of diethoxymethane. The reaction mixture liquid was then stirred for approximately 30 minutes at below −25° C. A vacuum (0.3 mm Hg) was applied to the reaction mixture for approximately 2.5 hours while the temperature of the reaction mixture was maintained at a temperature between about −24° C. and about −20° C., and afforded approximately 122.8 grams of a crude liquid product in two dry ice traps connected in series (used throughout the examples to collect the product unless otherwise specified). GC analysis using a RTX-200 (trifluoropropylmethyl polysiloxane stationary phase) capillary column (used for GC analysis throughout the examples unless otherwise specified) of the obtained liquid determined that the crude product was 38.0% compound A and 58.5% diethoxymethane. Fractional distillation of the obtained liquid using a ¾ inch×12 inch vacuum jacketed glass column which was packed with 3 mm glass helices and topped with an automatic splitter head with a condenser cooled to about 5° C. yielded the following fractions having a boiling point of about 45° C. (the desired vinyl ether purity is reported in parenthesis): Fraction 1: 2.8 grams (99.78%); Fraction 2: 55.3 grams (99.96%); and Fraction 3: 6.0 grams (99.93%).

The product yield for >99% pure sevoflurane compound A based on these three fractions was about 50% and it took only four days (one day for the reaction and three days for the distillation) to obtain sevoflurane compound A at the desired purity level. Using these methods, it is expected that it would take less than 15 days to obtain the quantity of sevoflurane compound A (at the desired purity level) achieved in Comparative Example 1.

NMR was performed on a mixture of Fractions 2 and 3 and the resulting spectra were consistent with literature data, thereby confirming formation of the expected fluorinated vinyl ether product.

$^1$H (CDCl$_3$): δ 5.41 (d, J=54.0 Hz, CH$_2$F).
$^{19}$F (proton decoupled): δ −66.39 (dd, J=22.6 Hz, J=2.8 Hz, J=8.5 Hz, CF$_3$), δ −85.24 (m) and δ −92.68 (m) for nonequivalent Fs of =CF$_2$, δ −152.76 (md, J=14.1 Hz, CH$_2$F).
$^{13}$C (proton decoupled): δ 103.33 (td, J=229.4 Hz, J=3.0 Hz, CH$_2$F), δ ~109 (m, C), δ 120.39 (tq, J=272.4 Hz, J=6.8 Hz, CF$_3$), δ 157.16 (mt, J=298.9 Hz, =CF$_2$).

Example 1b

Preparation of fluoromethyl 1,1,1,3,3-pentafluoro-2-propenyl ether (CF$_3$C(=CF$_2$)OCH$_2$F)

In a reaction similar to Example 1a, about 30.0 grams of sevoflurane (0.15 mols) was placed in a 250-mL 3-neck flask under nitrogen, and cooled in a dry ice-acetone bath to about −0.1° C. Approximately 50 mL of a 3.0 M solution of CH$_3$Li/CH$_2$(OC$_2$H$_5$)$_2$ (0.15 mols of the base) was added to the sevoflurane over about 2 hours and 38 minutes while maintaining a reaction temperature between about −8° C. and about +9° C. A violent, exothermic reaction was observed. The reaction mixture was then stirred at about −2° C. to about +6° C. for an additional 30 minutes. A vacuum (3.3 mm Hg) applied to the reaction mixture for approximately 2 hours, 17 minutes while the reaction mixture was held at a temperature between about −30° C. and about −17° C. yielded about 17.9 grams of a crude liquid product. The crude liquid contained 17.9% sevoflurane compound A, 70.6% CH$_2$(OC$_2$H$_5$)$_2$, and other side products.

Although sevoflurane compound A at the desired purity could be isolated according to this example, this example demonstrated that relatively higher reaction temperatures are generally not favorable for the product yield.

Example 1c

Preparation of fluoromethyl 1,1,1,3,3-pentafluoro-2-propenyl ether (CF$_3$C(=CF$_2$)OCH$_2$F)

About 20 grams of sevoflurane (0.10 mols) was placed in a reaction vessel and cooled to about −31.5° C. under a nitrogen atmosphere. Approximately 10 mL of a 3.0 M solution of CH$_3$Li/CH$_2$(OC$_2$H$_5$)$_2$ (0.03 mols of the base) was added over 48 minutes while maintaining a temperature between about −25° C. and about −41° C. A fast reaction was observed including formation of a white precipitate and gas evolution (methane). The reaction mixture was then cooled to about −51.5° C. and the remaining 40 mL of CH$_3$Li/CH$_2$(OC$_2$H$_5$)$_2$ (0.12 mols of the base) was added over 1 hour, 17 minutes, while maintaining a temperature between about −51.5° C. and about −40° C. The second addition of CH$_3$Li/CH$_2$(OC$_2$H$_5$)$_2$ caused a considerably slower reaction. The reaction mixture was then stirred at for 30 minutes at a temperature between about −43° C. and about −29° C. A vacuum (4.2 mmHg) applied to the reaction mixture for approximately 2 hours, 8 minutes while the reaction mixture was held at a temperature between about −33° C. and about −14° C. yielded about 2.1 grams of a crude liquid product. The crude product contained about 5.6% compound A, 81.1% diethoxymethane, and the remainder comprised unknown compounds. Acetone and then water were added to the residue of the reaction mixture. No reaction was observed, indicating that all of the CH$_3$Li reagent had been consumed.

Although sevoflurane compound A at the desired purity could be isolated according to this example, this example demonstrated that a relatively large excess of the organolithium base relative to the amount of fluorinated ether substrate is generally not favorable for the product yield.

Example 1d

Preparation of fluoromethyl 1,1,1,3,3-pentafluoro-2-propenyl ether (CF$_3$C(=CF$_2$)OCH$_2$F)

30 grams of sevoflurane (0.15 mols) was cooled to about −36.2° C. under nitrogen. Approximately 10 mL of a 3.0 M solution of CH$_3$Li/CH$_2$(OC$_2$H$_5$)$_2$ (0.03 mols of the base) was added over 29 minutes while maintaining a temperature between about −37.5° C. and about −30.5° C. After addition of the methyl lithium was complete, the addition funnel was washed with a few mL of diethoxymethane. The reaction mixture was then stirred for approximately 20 minutes at a temperature between about −39° C. and about −35° C. A vacuum (0.3 mmHg) applied to the reaction mixture for approximately 1 hour, 46 minutes while the reaction mixture was held at a temperature between about −38.5° C. and about 10.7° C. afforded approximately 30.0 grams of a crude liquid product. GC analysis of this liquid showed it contained 22.8% compound A, 47.1% unreacted sevoflurane, and 29.7% diethoxymethane.

Isolating the desired compound A product at high purity levels, however, would be difficult because of the presence of a significant amount of unreacted sevoflurane in the crude reaction product.

Example 2

Preparation of methyl 1,1,1,3,3-pentafluoro-2-propenyl ether, (CF$_3$C(=CF$_2$)OCH$_3$ or "SME olefin")

116.4 grams of methyl 1,1,1,3,3-hexafluoro-2-propyl ether (SME, 0.64 mols) was placed in a 250-mL 3-neck flask under a nitrogen atmosphere and cooled to about −35° C. in a dry ice-acetone bath. 250 mL of a solution of 3.0 M CH$_3$Li in diethoxymethane (0.75 mols of the base) was added gradually to the solution over approximately 2 hours, 54 minutes. The reaction mixture was then stirred for approximately 30 minutes at a temperature between about −35° C. and about −30° C. A vacuum (0.3 mm Hg) applied to the reaction mixture for approximately 3.5 hours while the reaction mixture was held at a temperature between −35° C. and about −30° C. yielded about 119.2 g grams of a crude liquid product. GC analysis of the crude liquid product demonstrated that the crude product contained 36.1% of the desired vinyl ether product (i.e, methyl 1,1,1,3,3-pentafluoro-2-propenyl ether), 0.4% of unreacted starting material (i.e., methyl 1,1,1,3,3,3-hexafluoro-2-propyl ether or SME), 57.7% CH$_2$(OC$_2$H$_5$)$_2$, and other impurities.

The above described reaction was repeated two more times using the following amounts of SME and 3.0 M solution of methyl lithium in diethoxymethane:
(i) SME (50.1 grams, 0.27 mols) and $CH_3Li/CH_2(OC_2H_5)_2$ (105 mL, 0.32 mols of the base), and
(ii) SME (118.1 grams, 0.65 mols) and $CH_3Li/CH_2(OC_2H_5)_2$ (255 mL, 0.77 mols of the base).

Crude products obtained from these reactions were shown by GC analysis to have comparable compositions. The crude products from the three reactions were combined (275.0 grams) and GC analysis demonstrated that the combined crude product had a composition of 36.4% of the desired vinyl ether product, 0.5% SME, 57.2% $CH_2(OC_2H_5)_2$, and other impurities. The combined crude product was distilled as described in Example 1 to give the following fractions: Fraction 1: 33° C., 8.7 grams, 99.7% of the desired vinyl ether product; Fraction 2: 33-34° C., 116.4 grams, 99.8% of the desired vinyl ether product; Fraction 3: 33-38° C., 14.9 grams, 99.7% of the desired vinyl ether product; Fraction 4: 38-54° C., 2.8 grams, 61.3% of the desired vinyl ether product, 36.5% SME, and other impurities; Fraction 5: 54-76° C., 5.5 grams, 4.0% of the desired vinyl ether product, 14.2% SME, and other impurities. The isolated yield of the desired vinyl ether product (based on these fractions) was about 55.9% (or about 55.2% for >99.7% purity).

The product yield for >99% pure methyl 1,1,1,3,3-pentafluoro-2-propenyl ether based on these five fractions was about 55.2% and it took only eight days (three days for the reaction and five days for the distillation) to obtain the desired vinyl ether product at the desired purity level.

NMR was performed on Fraction 2 and the resulting spectra confirmed the presence of the desired vinyl ether product.
$^1H$ ($CDCl_3$): $\delta$ 3.75 (s, $OCH_3$).
$^{19}F$ (proton decoupled): $\delta$ −66.78 (d, J=22.6 Hz, $CF_3$), $\delta$ −90.02 (dq, J=42.4 Hz, J=8.5 Hz) and $\delta$ −96.84 (dq, J=42.4 Hz, J=22.6 Hz) belong to 2 non-equivalent Fs of $=CF_2$.
$^{13}C$ (proton decoupled): $\delta$ 62.21 (t, J=3.0 Hz, $OCH_3$), $\delta$ 112.16 (m, quaternary C), $\delta$ 120.95 (ddq, J=272.4 Hz, J=7.2 Hz, J=9.8 Hz, $CF_3$), $\delta$ 156.52 (qt, J=301.9 Hz, J=3.8 Hz, $=CF_2$).
GC/MS: m/z: 162 ($M^+$), 69 ($CF_3^+$, base peak).

Example 3

Preparation of chloromethyl 1,1,1,3,3-pentafluoro-2-propenyl ether ($CF_3C(=CF_2)OCH_2Cl$ or "ClSevo olefin")

57.5 grams of chlorosevomethyl ether (ClSevo, 0.27 mols) dissolved in diethoxyethane (10 mL) was placed in a reaction vessel and pre-cooled under nitrogen to about −40° C. using a dry ice-acetone bath. 105 mL of a solution of 3.0 M $CH_3Li$ in diethoxymethane (0.32 mols of the base) was gradually added to the solution. Because gas evolution, initially occurred slowly, the reaction vessel temperature was increased to about −31° C. After approximately 10 mL of the $CH_3Li/CH_2(OC_2H_5)_2$ solution was added, the reaction occurred at a faster rate and addition of the methyl lithium base was complete in about 2 hours, 36 minutes. The reaction mixture was then stirred for approximately 35 minutes at a temperature between about 40° C. and about −33° C. A vacuum (5 mm Hg) applied to the reaction mixture for approximately 4 hours while the reaction mixture was held at a temperature between about −30° C. and about −3° C. yielded about 69.2 grams of a crude liquid product. GC analysis demonstrated that the crude product contained 12.9% of the desired vinyl ether product, 0.01% ClSevo, 83.0% $CH_2$ $(OC_2H_5)_2$, and other impurities. Fractional distillation of the crude product using a ¾"×12" vacuum jacketed glass column which was packed with 3 mm glass helices and topped with an automatically controlled splitter connected to a condenser cooled to about 5° C. gave the following fractions: Fraction 1: 70-72° C., 6.5 grams, 96.8% of the desired vinyl ether product (chloromethyl 1,1,1,3,3-pentafluoro-2-propenyl ether), 0.7% $CH_2(OC_2H_5)_2$; Fraction 2: 72-73° C., 8.9 grams, 97.3% of the desired vinyl ether product, 1.5% $CH_2(OC_2H_5)_2$; Fraction 3: 73-75° C., 2.2 grams, 88.2% of the desired vinyl ether 10.1% $CH_2(OC_2H_5)_2$; Fraction 4: 75-80° C., 1.3 grams, 60.3% of the desired vinyl product, 37.7% $CH_2(OC_2H_5)_2$. The isolated yield was 33.8% (29% at approximately 97% purity).

The product yield for >97% pure chloromethyl 1,1,1,3,3-pentafluoro-2-propenyl ether based on these four fractions was about 29% and it took only eight days (three days for the reaction and five days for the distillation) to obtain the desired vinyl ether product at the desired purity level.

NMR was performed on Fraction 2 and the spectra confirmed the presence of the expected vinyl ether compound.
$^1H$ ($CDCl_3$): $\delta$ 5.58 (s, $OCH_2Cl$).
$^{19}F$ (proton decoupled): $\delta$ −64.74 (dd, J=22.6 Hz, J=8.5 Hz, $CF_3$), $\delta$ −83.25 (dq, J=28.2 Hz, J=8.5 Hz) and $\delta$ −91.84 (dq, J=28.2 Hz, J=22.6 Hz) belong to 2 non-equivalent Fs of $=CF_2$.
$^{13}C$ (proton decoupled): $\delta$ 80.16 (t, J=3.8 Hz, $OCH_2Cl$), $\delta$ 107.80 (m, quaternary C), $\delta$ 120.43 (ddq, J=273.2 Hz, J=9.1 Hz, J=6.8 Hz, $CF_3$), $\delta$ 157.16 (qdd, J=299.6 Hz, J=299.6, J=3.0 Hz, $=CF_2$).
GC/MS: m/z: 196 ($M^+$), 198 ($M^+$+2), 69 ($CF_3^+$, base peak).

Example 4

Preparation of difluoromethyl 1-chloro-2,2-difluoroethenyl ether ($CF_2=CClOCHF_2$ or "chloro olefin")

About 133.2 grams of isoflurane (0.72 mols) was placed in a 1-L 3-neck flask equipped with a thermocouple, an addition funnel, a magnetic stirring bar, and a nitrogen inlet. The solution was cooled in a dry ice-acetone bath to about −31° C. About 270 mL of a 3.0 M solution of methyl lithium in diethoxymethane (0.81 mols of the base) was added to the flask over approximately 1 hour, 50 minutes while maintaining a reaction temperature between about −25° C. and about −20° C. After the methyl lithium addition was complete, the addition funnel was washed with a few mL of diethoxymethane and a long metal stick was used to dislodge solid on the glass wall. The reaction mixture was then stirred for approximately one hour at a temperature between about −25° C. and about −18° C. A vacuum (0.9 mmHg) applied to the reaction mixture for approximately 4 hours, 45 minutes while the reaction mixture was held to a temperature between about −32° C. and about −15° C. afforded about 109.6 grams of a crude liquid product. GC analysis using a packed column having a stationary phase of 1% SP-1000 (methyl silicon based stationary phase) demonstrated that the obtained liquid contained 33.1% chloro-olefin and 66.3% $CH_2(OC_2H_5)_2$.

A second reaction was similarly performed with 133.8 grams of isoflurane (0.73 mols) and 275 mL of a 3.0 M solution of $CH_3Li/CH_2(OC_2H_5)_2$ (0.83 mols of base). Addition of the base occurred over approximately 2 hours, 20 minutes, and the temperature was held between about −19° C. and about −26° C. The reaction mixture was then stirred for approximately one hour at about −19° C. to about −24° C. A vacuum (1.2 mmHg) applied to the reaction mixture for approximately 2 hours while the reaction mixture held to a temperature between about −16° C. and about −22° C. yielded about 139.5 grams of a crude liquid product. GC analysis using a 1% SP-1000 packed column demonstrated that the liquid contained 32.7% chloro-olefin and 66.8% $CH_2(OC_2H_5)_2$.

The crude products (from both reactions) were combined and GC analysis using a RTX-200 capillary column demonstrated the crude product contained 22.9% of the desired chloro olefin product and 3.7% of an unknown impurity having a close retention time. The peak for the unknown impurity overlapped with the olefin peak when a 1% SP-1000 packed column was used.

A third reaction was similarly performed with 133.7 grams of isoflurane (0.73 mols) and 260 mL of a 3.0 M solution of $CH_3Li/CH_2(OC_2H_5)_2$ (0.78 mols of the base). GC analysis using a 1% SP-1000 packed column demonstrated that the collected liquid product (169.3 g) contained 1.2% unreacted isoflurane. The liquid product was stored in a refrigerator overnight. 50.3 additional grams of isoflurane (0.27 mols) were added to the crude product liquid the next day, and then 155 mL of additional methyl lithium reagent (0.46 mols) was added to react with the additional isoflurane. A final crude product (135.9 g) was obtained. GC analysis using a RTX-200 capillary column demonstrated that the crude product contained 22.1% chloro-olefin, 5.5% unknown impurity, and 68.9% $CH_2(OC_2H_5)_2$.

The crude product liquids from the three batches were combined (about 391.5 grams total) and fractionally distilled on a ¾ inch×31 inch silvered, vacuum jacketed glass column which was packed with 3 mm glass helices and topped with an automatic reflux control head connected to a condenser cooled to about 4° C. The following fractions were collected and analyzed by GC (RTX-200 capillary column): Fraction 1: 7.5 grams at 38.5° C., 93.4% chloro-olefin, 3.3% unknown impurity; Fraction 2: 11.7 grams at 39.5° C., 94.2% chloro-olefin, 3.4% unknown impurity; Fraction 3: 30.7 grams at 41° C., 89.4% chloro-olefin, 9.8% unknown impurity; Fraction 4: 106.6 grams at 39.5° C., 86.2% chloro-olefin, 12.9% unknown impurity; Fraction 5: 18.6 grams at 40-39° C., 81.0% chloro-olefin, 17.6% unknown impurity.

Fractions 1 through 4 were combined (152.6 g) and a second distillation was performed on the combined fractions using a ¼ inch×12 inch vacuum jacketed glass column which was packed with 3 mm glass helices and topped with an automatic reflux splitter with a condenser cooled to about 5° C. The following fractions were obtained and their purity was analyzed by GC (RTX-200 capillary column): Fraction 1: 1.2 grams (yellow color) at 40° C., 94.6% chloro-olefin, 2.1% unknown impurity; Fraction 2: 31.0 grams at 40° C., 96.1% chloro-olefin, 3.3% unknown impurity; Fraction 3: 39.8 grams at 40-41° C., 95.7% chloro-olefin, 4.0% unknown impurity; Fraction 4: 29.3 grams at 41° C., 93.4% chloro-olefin, 6.1% unknown impurity; Fraction 5: 32.9 grams at 41° C., 85.1% chloro-olefin, 13.2% unknown impurity. The overall yield was 40.1%.

The product yield for >85% pure chloro-olefin based on these five fractions was about 34.8% and it took only nine days (three days for the reaction and six days for the distillation) to obtain the desired vinyl ether product at the desired purity level.

NMR was performed on fraction 2 and the spectra confirmed the presence of the expected compound.

$^1H$ ($CDCl_3$): δ 6.37 (t, J=72.0 Hz, $CHF_2$).

$^{19}F$ (proton decoupled): δ −85.92 (d, J=5.6 Hz, $CHF_2$), δ −94.53 (d, J=45.2 Hz) and δ −102.71 (td, J=5.6 Hz, J=45.2 Hz) from non-equivalent Fs of $=CF_2$.

$^{13}C$ (proton decoupled): δ 106.42 (tdd, J=38.5 Hz, J=49.1 Hz, J=5.3 Hz, C), δ 115.51 (t, J=269.4 Hz, $CHF_2$), δ 153.35 (dd, J=284.5 Hz, J=292.1 Hz, $=CF_2$).

Example 5

Preparation of difluoromethyl 1,2,2-trifluoroethenyl ether ($CF_2=CFOCHF_2$ or Des-olefin)

46.5 grams of desflurane (0.28 mols) was placed in a 250 mL 3-neck flask and cooled to about −47° C. under a nitrogen atmosphere. 105 mL of a 3.0 M solution of $CH_3Li$ in $CH_2(OC_2H_5)_2$ (0.32 mols of the base) was added to the reaction flask over approximately 2 hours and 30 minutes while the temperature was held between about −50° C. and about −25° C. The reaction mixture was then stirred at for approximately 30 minutes at a temperature between about −40° C. and about −37° C. A vacuum (0.7 mmHg) applied to the reaction mixture for approximately 2 hours while the reaction mixture was held at a temperature between about −35° C. and about −20° C. yielded 26.8 grams of a liquid containing 11.0% des-olefin, 9.0% unreacted desflurane, and 61.1% $CH_2(OC_2H_5)_2$ (as demonstrated by GC analysis using a RTX-200 capillary column).

The same procedure was repeated using 81.0 grams of desflurane (0.48 mols) and 185 mL of a 3.0 M solution of $CH_3Li$ in $CH_2(OC_2H_5)_2$ (0.56 mols). A crude product liquid (101.1 g) was collected containing 6.7% olefin, 6.0% desflurane, and 72.7% $CH_2(OC_2H_5)_2$.

Crude products from the two reactions were combined and fractionally distilled on the apparatus used in Example 1 yielding the following fractions: Fraction 1: 10-12° C., 4.2 grams, 96.1% des-olefin, 2.4% desflurane, and other impurities; Fraction 2: 12-14° C., 1.6 grams, 91.5% des-olefin, 7.6% desflurane, and other impurities; Fraction 3: 11-13° C., 0.5 grams, 96.4% des-olefin, 3.0% desflurane, and other impurities; Fraction 4: 19-25° C., 16.8 grams, 45.9% des-olefin, 52.6% desflurane, and other impurities. The yield was 12.2% based on the above fractions.

The product yield for 96% pure des-olefin based on these four fractions was about 10.9% and it took four days (two days for the reaction and two days for the distillation) to obtain the desired vinyl ether product in the desired purity.

NMR analysis was performed on Fraction 1 and the spectra confirmed the presence of the expected fluorinated vinyl ether product, $CF_2=CFOCHF_2$:

$^1H$ ($CDCl_3$): δ 6.42 (dt, J=3.0 Hz, J=72.0 Hz, $CHF_2$).

$^{19}F$ (proton decoupled): δ −84.39 (d, J=5.6Hz) and δ −84.41 (d, J=5.6Hz), non-equivalent Fs of $CHF_2$; δ −115.98 (mdd, J=90.4 Hz, J=62.1 Hz) and δ −124.18 (mdd, J=93.2 Hz, J=108.7 Hz), non-equivalent Fs of $=CF_2$; δ −134.82 (mdd, J=63.5 Hz, J=113.0 Hz, $=CFO$).

$^{13}C$ (proton decoupled): δ 115.06 (t, J=270.9 Hz, $CHF_2$), δ 130.89 (dtd, J=264.9Hz, J =46.8 Hz, J=4.5 Hz, $=CF$), δ 146.95 (ddt, J=56.6 Hz, J=3.8 Hz, J=278.5 Hz, $=CF_2$).

The same reaction was repeated with 65.5 grams of desflurane (0.39 mols) and 160 mL of a 3.0 M solution of $CH_3Li$ in $CH_2(OC_2H_5)_2$ (0.48 mols) to yield 87.5 g of crude product liquid containing 14.0% olefin, 14.9% unknown, 64.9% $CH_2(OC_2H_5)_2$, and other impurities (as demonstrated by GC analysis using a RTX-200 capillary column). Fractional distillation afforded a des-olefin yield of 18.4%, and a by-product ($CF_2=C(CH_3)OCHF_2$) yield of 27.6%. The structure of the by-product was identified by NMR on a 99.3% pure fraction (bp 46° C.):

$^1H$ ($CDCl_3$): δ 1.90 (t, J=3.0 Hz, $CH_3$), δ 6.27 (t, J=72.0 Hz, $CHF_2$).

$^{19}$F (proton decoupled): δ −82.32 (d, J=5.6 Hz, CHF$_2$); δ −98.26 (dd, J=59.3 Hz, J=5.6 Hz) and δ −110.81 (d, J=62.1 Hz), non-equivalent Fs of =CF$_2$.

$^{13}$C (proton decoupled): δ 12.59 (s, CH$_3$), δ 108.24 (mdd, J=48.3 Hz, J=15.1 Hz, C), δ 115.82 (mt, J=266.4 Hz, CHF$_2$), δ 154.86 (dd, J=280.0 Hz, J=289.0 Hz, =CF$_2$).

Example 6

Preparation of bis(1,2,2-trifluoroethenyl)ether (CF$_2$=CFOCF=CF$_2$ or bis-olefin) and 1,2,2,2-tetrafluoroethyl 1,2,2-trifluoroethenyl ether (CF$_2$=CFOCHFCF$_3$ or mono-olefin))

65.8 grams of bis-(1,2,2,2-tetrafluoroethyl)ether (0.30 mols) was cooled to about −30° C. under a nitrogen atmosphere. 100 mL of a 3.0 M solution of CH$_3$Li in CH$_2$(OC$_2$H$_5$)$_2$ (0.30 mols of the base) was added to the reaction solution over approximately 2 hours, 36 minutes, while maintaining a reaction temperature between about −15° C. and about −36° C. The reaction mixture was then stirred for about 30 minutes at a temperature between about −28° C. and about −26° C. A vacuum (0.3 mmHg) applied to the reaction mixture for approximately 4 hours, 5 minutes while the reaction mixture was maintained at a temperature between about −18° C. and about −15° C. gave about 79.5 grams of a crude liquid product.

The same experiment was repeated once more and afforded about 80.1 grams of additional crude liquid product. Both liquids were combined and GC analysis demonstrated that the crude product contained 2.6% of the anticipated bis-olefin product, 7.5% of the anticipated mono-olefin product, 8.4% unreacted ether starting material, 8.1% of a major by-product (1-methyl-2,2-difluoroethenyl 1,2,2,2-tetrafluoroethyl ether, CF$_2$=C(CH$_3$)OCHFCF$_3$), and 72.1% CH$_2$(OC$_2$H$_5$)$_2$.

Fractional distillation of the combined liquid yielded 15 fractions with various compositions. Fractions 1 & 2 had 95.4% and 93.2% of bis-olefin, respectively. However, the bis-olefin polymerized shortly after isolation. The calculated yields based on the distilled fractions are: 4.4% of bis-(1,2,2-trifluoroethenyl)ether (CF$_2$=CFOCF=CF$_2$), 19.2% of 1,2,2,2-tetrafluoroethyl 1,2,2-trifluoroethenyl ether (CF$_2$=CFOCHFCF$_3$), and 13.4% of the major by-product, 1-methyl-2,2-difluoroethenyl 1,2,2,2-tetrafluoroethyl ether (CF$_2$=C(CH$_3$)OCHFCF$_3$).

NMR was performed on Fraction 1 and Fraction 3, which contained 35.8% bis-olefin and 61.8% mono-olefin and spectra confirmed the presence of CF$_2$=CFOCF=CF$_2$ (bp 20-21° C.):

$^{19}$F (CDCl$_3$, proton decoupled): δ −118.50 (dd, J=96.0 Hz, J=62.1 Hz,) and δ −124.72 (dd, J=113.0 Hz, J=65.0 Hz) belong to non-equivalent Fs of CF$_2$, δ −138.69 (dd, J=110.1 Hz, J=65.0 Hz, =CF).

$^{13}$C (proton decoupled): δ 134.6 (td, J=270 Hz, J=50 Hz, =CF), δ 145.56 (tdd, J=277.7 Hz, J=54.3 Hz, J=3.0 Hz, =CF$_2$).

NMR was also performed on Fraction 5, which contained 96.5% mono-olefin (CF$_2$=CFOCHFCF$_3$, bp 29-30° C.), and the spectrum confirmed the presence of this product:

$^1$H (CDCl$_3$), 5.66 (d, J=54.0 Hz, OCHF).

$^{19}$F (proton decoupled): δ −84.18 (d, J=5.6 Hz, CF$_3$), δ −117.45 (dd, J=62.1 Hz, J=90.4 Hz) and δ −124.63 (ddd, J=113.0 Hz, J=91.8 Hz, J=2.8 Hz) belong to non-equivalent Fs of =CF$_2$, δ −138.12 (dq, J=62.1 Hz, J=8.5 Hz, CHF), δ −145.32 (m, =CFO).

$^{13}$C (proton decoupled): δ 102.15 (dqdd, J$_{doublet}$=243.8 Hz, J$_{quartet}$=41.5 Hz, CHF), δ 118.32 (qd, J=281.5 Hz, J=30.2 Hz, CF$_3$), δ 134.04 (ddd, J=268.7 Hz, J=44.5 Hz, J =48.3 Hz, =CF), δ 145.99 (tdd, J=277.7 Hz, J=56.6 Hz, J=3.0 Hz, =CF$_2$).

NMR was also performed on Fraction 14, which contained 95.6% of the major by-product (CF$_2$=C(CH$_3$)OCHFCF$_3$, bp 68-70° C.), and the spectrum confirmed the presence of this by-product:

$^1$H (CDCl$_3$): δ 1.91 (dd, J=3.0 Hz, J=6.0 Hz, CH$_3$), δ 5.46 (dq, J=57.0 Hz, J=3.0 Hz, CHF).

$^{19}$F (proton decoupled): δ −84.40 (dd, J=6.2 Hz, J=0.8 Hz, CF$_3$), δ −99.00 (dd, J=65.0 Hz, J=5.6 Hz) and δ −112.22 (d, J=65.0 Hz) belong to non-equivalent Fs of =CF$_2$, δ −141.31 (qd, J=5.6 Hz, J=5.6 Hz, CHF).

$^{13}$C (proton decoupled): δ 11.63 (d, J=0.8 Hz, CH$_3$), δ 102.96 (dqt, J=236.2 Hz, J=40.0 Hz, J=3.0 Hz, CHF), δ 112.86 (ddd, J=47.5 Hz, J=15.8 Hz, J=1.5 Hz, C), δ 118.90 (qd, J=281.5 Hz, J=32.5 Hz, CF$_3$), δ 154.53 (ddd, J=273.2 Hz, J=288.3 Hz, J=3.0 Hz, =CF$_2$).

Another reaction was performed under similar conditions using a 1:2 molar ratio of bis-(1,2,2,2-tetrafluoroethyl)ether (32.5 grams, 0.15 mols) and CH$_3$Li (105 mL of 3.0 M solution of CH$_3$Li in CH$_2$(OC$_2$H$_5$)$_2$, 0.32 mols of the base). 43.1 grams of a crude product liquid was collected. GC analysis demonstrated that the liquid contained 1.5% bis-olefin, 0.4% mono-olefin, 0.1% unreacted starting ether, 4.3% unknown by-product, 7.3% CF$_2$=C(CH$_3$)OCHFCF$_3$ (major by-product discussed above) and 84.5% CH$_2$(OC$_2$H$_5$)$_2$. These reaction conditions demonstrate that doubling the amount of the lithium reagent produces more of the by-product CF$_2$=C(CH$_3$)OCHFCF$_3$ at the expense of the desired mono-olefin.

Example 7

Preparation of difluoromethyl 2,2-difluoroethenyl ether (CF$_2$=CHOCHF$_2$ or difluoro-olefin)

Similar to Example 2, 40.5 grams of difluoromethyl 2,2,2-trifluoroethyl ether (CF$_3$CH$_2$OCHF$_2$, 0.27 mols) was reacted with a 100 mL of a 3.0 M solution of CH$_3$Li/CH$_2$(OC$_2$H$_5$)$_2$ (0.30 mols of the base) for approximately 2 hours, 28 minutes while maintaining a reaction temperature between about −17° C. and about −10° C. A vacuum applied to the reaction mixture for approximately 2 hours, 38 minutes while the reaction mixture was maintained at a temperature between about −23° C. and about −16° C. afforded 59.1 g of liquid, which contained 5.73% difluoro-olefin, 44.4% unreacted starting material, and 46.0% CH$_2$(OC$_2$H$_5$)$_2$ (as demonstrated by GC analysis). This liquid was fractionally distilled on a ½"×12" long vacuum jacketed glass column packed with 3 mm glass helices topped with an automatic splitter with a condenser cooled to 4° C. to give the following three fractions which were analyzed by GC: Fraction 1: 20-21.5° C., 1.0 grams, 81.0% difluoro-olefin, 9.9% starting material, and other impurities; Fraction 2: 30° C., 0.4 grams, 36.1% difluoro-olefin, 60.3% starting material, and other impurities; Fraction 3, 30-31° C., 6.3 grams, 4.1% difluoro-olefin, 95.5% starting material, and other impurities. The overall yield of the difluoro-olefin was 3.5%.

NMR was performed on Fraction 1 and the spectra confirmed the presence of the expected product:

$^1$H (CDCl$_3$): δ 6.03 (dd, J=3.0 Hz, J=15.0 Hz, =CHO), δ 6.29 (dt, J=3.0 Hz, J=72.0 Hz, CHF$_2$).

$^{19}$F (proton decoupled): δ −85.69 (d, J=2.8Hz, CHF$_2$), δ −94.14 (d, J=59.3Hz) and δ 112.27 (d, J=62.1 Hz) belong to non-equivalent Fs of =CF$_2$).

Example 8

Preparation of chlorodifluoromethyl 2,2-difluoroethenyl ether (CF$_2$=CHOCF$_2$Cl)

Following the same procedures as above, 24.5 grams of chlorodifluoromethyl 2,2,2-trifluoroethyl ether (0.13 mols) was reacted with 50 mL of a 3.0 M solution of CH$_3$Li/CH$_2$(OC$_2$H$_5$)$_2$ (0.15 mols of the base) over approximately 1 hour, 35 minutes while maintaining a reaction temperature between about −14° C. and −4° C. A vacuum applied to the reaction mixture for approximately 2.5 hours while the reaction mixture was maintained at a temperature between about −27° C. and −16° C. afforded 40.6 grams of liquid containing 1.4% the desired fluorinated vinyl ether product (chlorodifluoromethyl 2,2-difluoroethenyl ether), 38.1% unreacted ether starting material, and 55.4% CH$_2$(OC$_2$H$_5$)$_2$ (as demonstrated by GC analysis). The same reaction was repeated two more times using approximately the same amounts of reactants yielding 29.4 grams and 37.4 grams of a liquid crude product, respectively. The liquid crude products from the three reactions were combined. The mixed liquid was fractionally distilled, but failed to yield a pure fraction of the desired fluorinated vinyl ether. Fraction 2 (4.5 g) was collected at 24-39° C. and contained 21.3% chlorodifluoromethyl 2,2-difluoroethenyl ether and 69.8% of the ether starting material. The overall yield of chlorodifluoromethyl 2,2-difluoroethenyl ether was 1.7%.

Fraction 2 was analyzed by NMR and confirmed the presence of the desired fluorinated vinyl ether product:

$^1$H (CDCl$_3$): δ 6.05 (dd, J=3.0 Hz, J=15.0 Hz, =CH).

$^{19}$F (proton decoupled): δ −31.72 (s, CF$_2$Cl), δ −91.32 (d, J=50.8 Hz) and δ −110.14 (d, J =56.5 Hz) belong to nonequivalent Fs of =CF$_2$.

$^{13}$C (proton decoupled): δ 125.66 (t, J=290.6 Hz, overlapping with starting material peaks), δ 157.39 (dd, J=302.2 Hz, J=295.1 Hz, =CF$_2$). The =CH peaks could not be differentiated from the noise signal, due to low sample concentration and multiple splitting of the peak.

Numerous modifications and variations of the methods for preparing a fluorinated ether compound described herein are expected to occur to those skilled in the art in view of the accompanying disclosure. Consequently, only such limitations as appear in the appended claims should be placed on the invention.

What is claimed is:

1. A method for preparing a fluorinated vinyl ether compound, the method comprising:
    reacting a fluorinated ether substrate having (i) a hydrogen atom on a carbon atom that is alpha to an etheric oxygen and (ii) a fluorine atom on a carbon atom that is beta to the etheric oxygen, with an organolithium base to provide a reaction product comprising a fluorinated vinyl ether compound,
    wherein the reaction is performed in diethoxymethane, and the organolithium base is methyl lithium.

2. The method of claim 1, wherein the fluorinated ether substrate has the following formula (I):

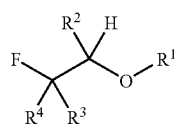

(I)

wherein R$^1$ is selected from the group consisting of alkyl and haloalkyl;
R$^2$ is selected from the group consisting of H, F, Cl, alkyl, and haloalkyl; and,
R$^3$ and R$^4$ are independently selected from the group consisting of H and F.

3. The method of claim 1, wherein the fluorinated ether substrate is selected from the group consisting of sevoflurane, sevomethyl ether, chlorosevomethyl ether, difluoromethyl 2,2,2-trifluoroethyl ether, isoflurane, desflurane, chlorodifluoromethyl 2,2,2-trifluoroethyl ether, and bis-(1,2,2,2-tetrafluoroethyl) ether.

4. The method of claim 1, wherein the fluorinated ether substrate is selected from the group consisting of sevoflurane, sevomethyl ether, chlorosevomethyl ether, desflurane, difluoromethyl 2,2,2-trifluoroethyl ether, and isoflurane.

5. The method of claim 1, wherein the fluorinated ether substrate has the following formula (II):

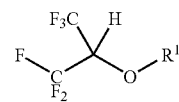

wherein R$^1$ is selected from the group consisting of alkyl and haloalkyl.

6. The method of claim 1, wherein the halogenated vinyl ether substrate is selected from the group consisting of sevoflurane, sevomethyl ether, and chlorosevomethyl ether.

7. The method of claim 1, wherein the concentration of methyl lithium in diethoxymethane is between about 0.10 M and about 4.0 M.

8. The method of claim 1, wherein the organolithium base has a concentration between about 15 molar percent ("mol %") and about 175 mol % relative to the amount of the fluorinated ether substrate.

9. The method of claim 1, wherein the organolithium base has a concentration between about 75 mol % and about 125 mol % relative to the amount of the fluorinated ether substrate.

10. The method of claim 1, further comprising cooling the fluorinated ether substrate to less than or equal to 5 ° C. and adding the organolithium base to the pre-cooled fluorinated ether substrate.

11. The method of claim 1, further comprising removing the fluorinated vinyl ether compound from the reaction product by applying a vacuum to the reaction product.

12. The method of claim 1, further comprising isolating the fluorinated vinyl ether from the reaction product by fractional distillation of the reaction product.

13. The method of claim 1, wherein the fluorinated vinyl ether has a purity of at least 95%.

14. The method of claim 1, wherein the reaction is performed under an inert atmosphere.

15. A method for preparing fluorinated vinyl ether compounds, the method comprising:
    providing a fluorinated ether substrate having a hydrogen atom on a carbon atom that is alpha to an etheric oxygen, and a fluorine atom on a carbon atom that is beta to the etheric oxygen;
    cooling the fluorinated ether substrate to less than or equal to 5 ° C.;
    adding methyl lithium dissolved in diethoxymethane to the fluorinated ether substrate to provide a reaction mixture; and, removing a fluorinated vinyl ether compound from the reaction mixture.

16. The method of claim 15, further comprising stirring the reaction mixture at a temperature that is less than or equal to 5° C. before removing the fluorinated vinyl ether compound.

17. The method of claim 15, wherein removing the fluorinated vinyl ether compound comprises applying a vacuum to the reaction mixture to provide a crude product containing the fluorinated vinyl ether compound and purifying the fluorinated vinyl ether compound by fractional distillation.

18. The method of claim 1, wherein the organolithium base has a concentration between about 105 mol % and about 125 mol % relative to the amount of the fluorinated ether substrate.

* * * * *